(12) United States Patent
Christy et al.

(10) Patent No.: US 12,013,317 B2
(45) Date of Patent: Jun. 18, 2024

(54) SAMPLING ZONE ISOLATION TOOL AND METHOD FOR GROUNDWATER SAMPLING SYSTEM

(71) Applicant: Kejr, Inc., Salina, KS (US)

(72) Inventors: Thomas M. Christy, Salina, KS (US); Jedidiah Eric Davis, Salina, KS (US)

(73) Assignee: Kejr, Inc., Salina, KS (US)

( * ) Notice: Subject to any disclaimer, the term of this patent is extended or adjusted under 35 U.S.C. 154(b) by 92 days.

(21) Appl. No.: 17/875,324

(22) Filed: Jul. 27, 2022

(65) Prior Publication Data
US 2023/0033731 A1     Feb. 2, 2023

Related U.S. Application Data

(60) Provisional application No. 63/226,105, filed on Jul. 27, 2021.

(51) Int. Cl.
*G01N 1/14*     (2006.01)
*G01N 33/18*    (2006.01)

(52) U.S. Cl.
CPC ........... *G01N 1/14* (2013.01); *G01N 33/1886* (2013.01)

(58) Field of Classification Search
CPC ................. G01N 1/14; G01N 33/1886; G01N 2001/1031; G01N 2001/1418
USPC .............. 73/863.23, 863.83, 863.84, 863.85, 73/864.34, 864.74
See application file for complete search history.

(56) References Cited

U.S. PATENT DOCUMENTS

| | | | |
|---|---|---|---|
| 5,503,031 | A | 4/1996 | Scott et al. |
| 5,612,498 | A | 3/1997 | Wittig et al. |
| 5,635,653 | A | 6/1997 | Wittig et al. |
| 6,877,965 | B2 | 4/2005 | McCall et al. |
| 7,735,553 | B2 | 6/2010 | Carlin et al. |

FOREIGN PATENT DOCUMENTS

HU      206756 B    * 12/1992    ........... E21B 43/082

OTHER PUBLICATIONS

Geoprobe Screen Point 16 Groundwater Sampler, Standard Operating Procedure, Technical Bulletin No. MK3142, Geoprobe Systems, Salina, KS, Nov. 2006.

* cited by examiner

*Primary Examiner* — Robert R Raevis
(74) *Attorney, Agent, or Firm* — Jeffrey L. Thompson; Thompson Law, P.A

(57) ABSTRACT

A screen point groundwater sampling system includes a drive head positioned between the upper end of a cylindrical housing and a lower end of a probe rod. A latching tool is provided to secure a mechanical pump to the drive head upon insertion of the latching tool into the inner bore of the drive head. The latching tool creates a water-tight seal between the drive head and the inlet of the mechanical pump to prevent contamination of the groundwater sample from water leaking into the probe rod string above the drive head. A frangible structure on the latching tool allows the mechanical pump to be removed from the drive head upon applying sufficient vertical force in an upward direction to shear the frangible structure. The latching tool can also be used to attach a sample tubing to the drive head for use with a pump located at the ground surface.

29 Claims, 9 Drawing Sheets

SAMPLING ZONE ISOLATION TOOL AND METHOD FOR GROUNDWATER SAMPLING SYSTEM

RELATED APPLICATIONS

This application claims the benefit of U.S. Provisional Patent Application No. 63/226,105 filed on Jul. 27, 2021, the contents of which are incorporated herein by reference.

BACKGROUND OF THE INVENTION

Field of the Invention

The present invention relates generally to devices for obtaining water samples from below the surface of the ground, and in particular, to screen point sampling systems for obtaining groundwater samples.

Description of the Related Art

Screen point (SP) groundwater sampling systems are described in Applicant's U.S. Pat. Nos. 5,503,031, 5,612,498 and 5,635,653. The screen point sampling system includes an elongated hollow screen telescopically received within an elongate cylindrical housing. The screen is in a stowed position while the device is driven into the ground, and in a deployed position extending out of the lower end of the housing to collect groundwater. An expendable drive point is positioned at the lower end of the device to facilitate driving the device into the ground.

The screen point sampling system has some limitations that the present invention will solve. For example, leakage in the rod string above the drive head can contaminate the groundwater sample, sealing the rods is difficult, and static water inside the rods can sometimes mix with the water sample being pumped.

There is a need in the industry for a groundwater sampling system that allows groundwater to be collected with reduced risk of contamination from static water within the probe rod string.

SUMMARY OF THE INVENTION

An object of the present invention is to provide a groundwater sampling system with a sealing structure for keeping static water within the probe rod string separate and isolated from the groundwater being collected.

A further object of the present invention is to provide a groundwater sampling system with a latching tool that can be inserted down the bore of the probe rod string and into a latched condition with the drive head.

A further object of the present invention is to provide a latching tool that can be used to secure a mechanical pump or a sample tubing to the drive head with a sealed barrier between the groundwater being collected and the static water within the probe rod string.

A further object of the present invention is to provide an improved method for sampling groundwater with a screen point sampling assembly that includes inserting a structure with a latching tool down through the probe rod to secure a mechanical pump or a sample tubing to the drive head, and removing the inserted structure and latching tool after the groundwater sample is pumped by applying sufficient force to release the latching tool.

A further object of the present invention is to provide a latching tool for use in a screen point sampling system to secure a lower portion of an inserted mechanical pump to a drive head while allowing an upper portion of the mechanical pump to be actuated by vertical forces applied to sample tubing connected to the pump.

To accomplish these and other objects of the present invention, a screen point groundwater sampling system is provided that includes a drive head positioned between the upper end of a cylindrical housing and a lower end of a probe rod. A latching tool attached to a lower end of a mechanical pump is provided to secure the mechanical pump to the drive head upon insertion of the latching tool into the inner bore of the drive head. The latching tool creates a water-tight seal between the inner bore of the drive head and the inlet of the mechanical pump to prevent contamination of the groundwater sample from water leaking into the probe rod string above the drive head. A frangible structure on the latching tool allows the mechanical pump to be removed from the drive head upon applying sufficient vertical force in an upward direction to shear the frangible structure. The latching tool can also be used to attach a sample tubing to the drive head for use with a pump located at the ground surface.

According to one aspect of the present invention, a combination of a drive head and a latching tool for a groundwater sampling system is provided. The drive head has an upper threaded portion adapted to be attached to a lower end of a probe rod, a lower threaded portion adapted to be attached to an upper end of an elongated screen sheath, and an inner bore. The latching tool is adapted to be attached to a lower end of an inserted structure for securing the inserted structure to the drive head. The latching tool has a latch for engaging the drive head upon insertion of the latching tool into the inner bore of the drive head.

According to another aspect of the present invention, a latching tool for securing an inserted structure to a drive head in a screen point sampling system is provided, the latching tool comprising: a main body having a generally cylindrical outer surface with at least one groove for receiving an O-ring seal to create a seal between the outer surface of the latching tool and an inner surface of the drive head; an outer shoulder for engaging a structure in the inner bore of the drive head to limit downward movement of the latching tool through the drive head; an inner bore for providing fluid passage from an elongated screen sheath below the drive head to the inserted structure; and a pivotally mounted latch member adapted to engage the drive head upon insertion of the latching tool into the inner bore of the drive head.

According to another aspect of the present invention, a method of sampling groundwater is provided, comprising: driving a screen point sampling assembly into the ground, the screen point sampling assembly comprising a drive head connected between a lower end of a probe rod and an upper end of an elongated screen sheath, the drive head having an inner bore; deploying a screen from the elongated screen sheath; inserting a structure with a latching tool downward through the probe rod until the latching tool engages a downward limiting structure on the drive head, an outer surface of the latching tool is sealed with the inner bore of the drive head, and a latch of the latching tool flips into a position to restrict upward movement of the latching tool relative to the drive head; actuating a pump to pump groundwater through an inner bore of the latching tool while the outer surface of the latching tool remains sealed with the inner bore of the drive head and the latch restricts upward movement of the latching tool relative to the drive head; and removing the inserted structure and latching tool from the probe rod and drive head by applying sufficient force to cause a frangible structure on the latching tool to shear.

Numerous other objects of the present invention will be apparent to those skilled in this art from the following description wherein there is shown and described embodiments of the present invention, simply by way of illustration of some of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the present invention is made with reference to the accompanying drawings. In the drawings.

DETAILED DESCRIPTION OF THE INVENTION

A screen point groundwater sampling system 10 having a latching tool 11 according to the present invention will now be described with reference to FIGS. 1 to 9 of the accompanying drawings.

Figure 1:
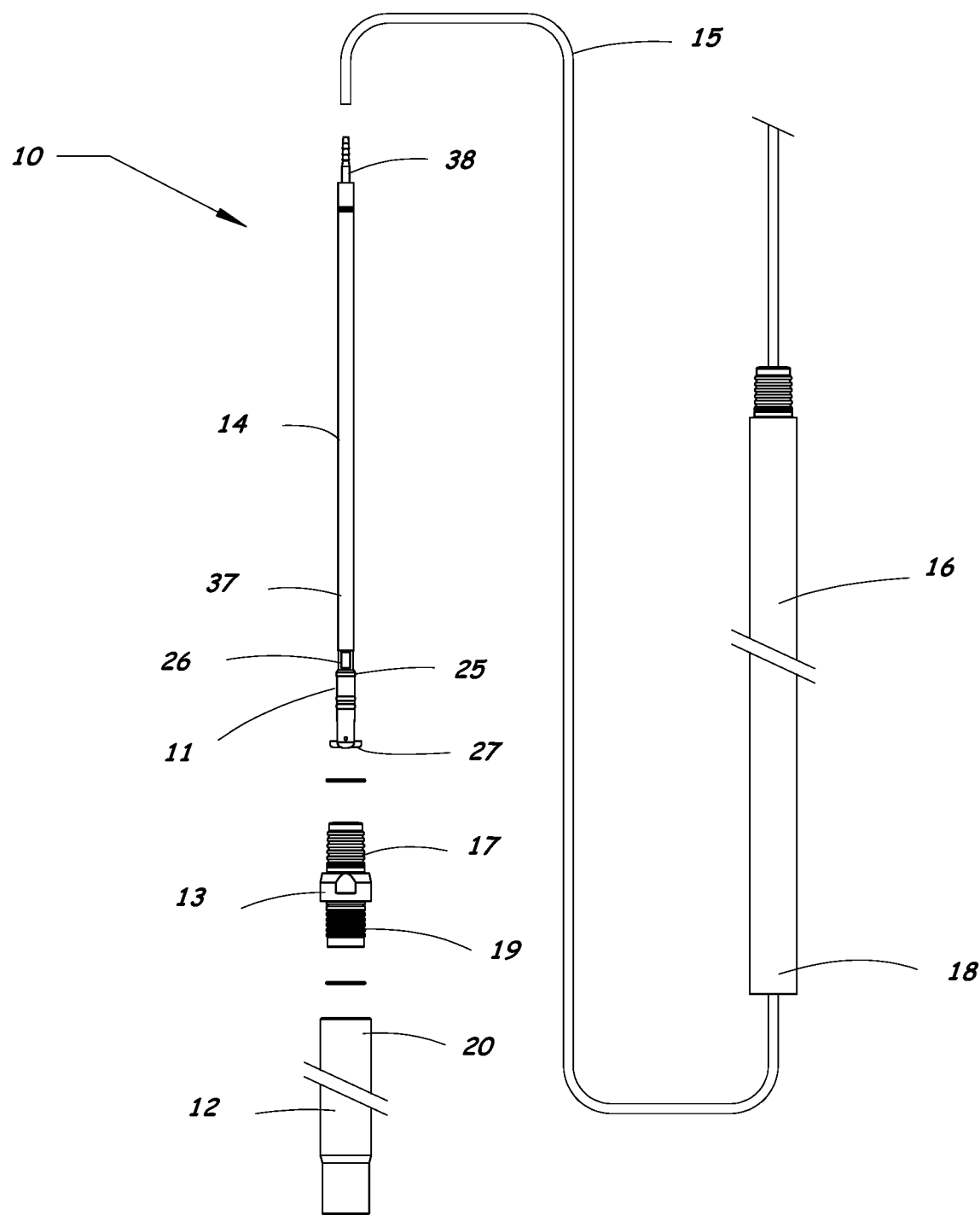
FIG. 1 is an exploded view of a screen point groundwater sampling system according to the present invention.
Figure 2:
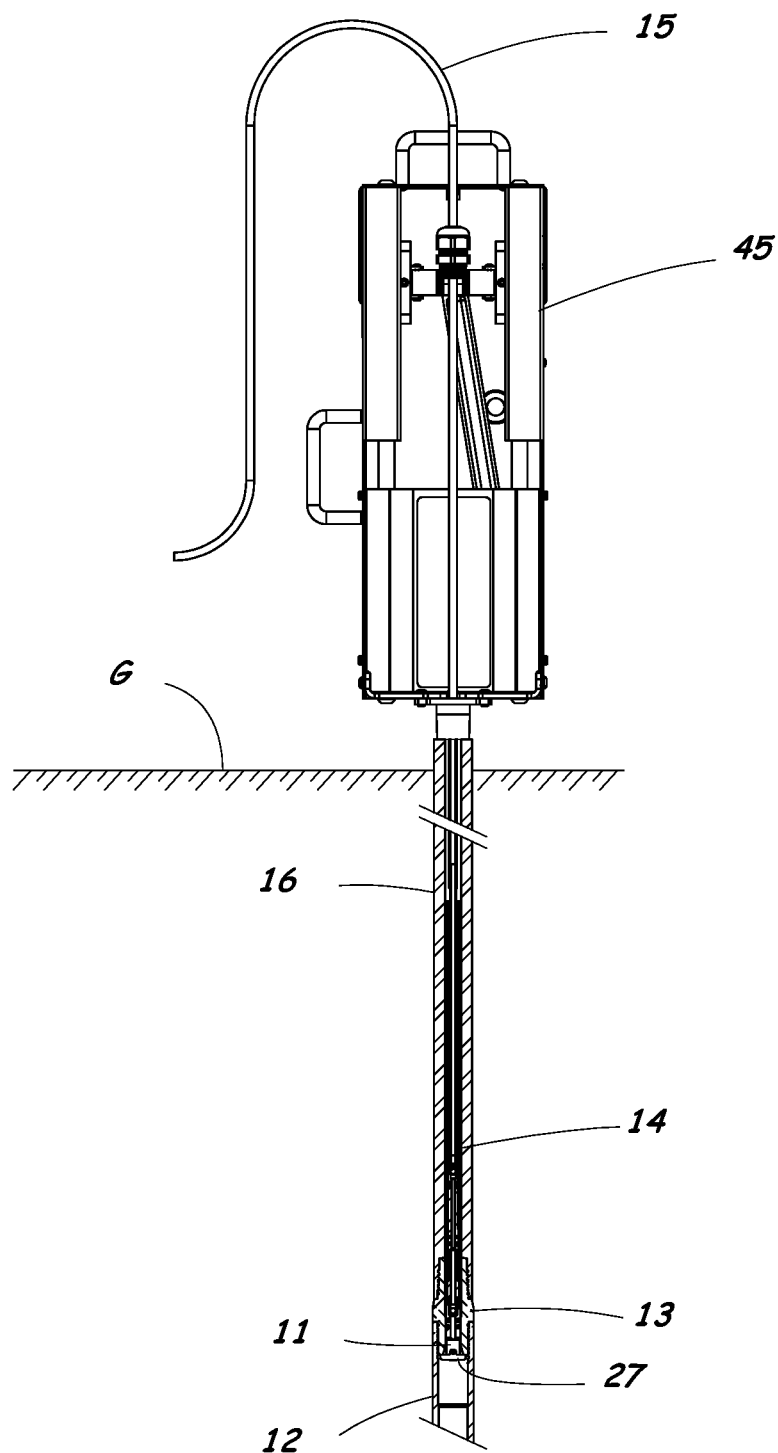
FIG. 2 is an elevation view of the screen point groundwater sampling system with a mechanical pump inserted through the probe rod and latched to the drive head, and an actuator located above ground for applying vertical forces to a sample tubing connected to the mechanical pump for actuating the pump.
Figure 3:
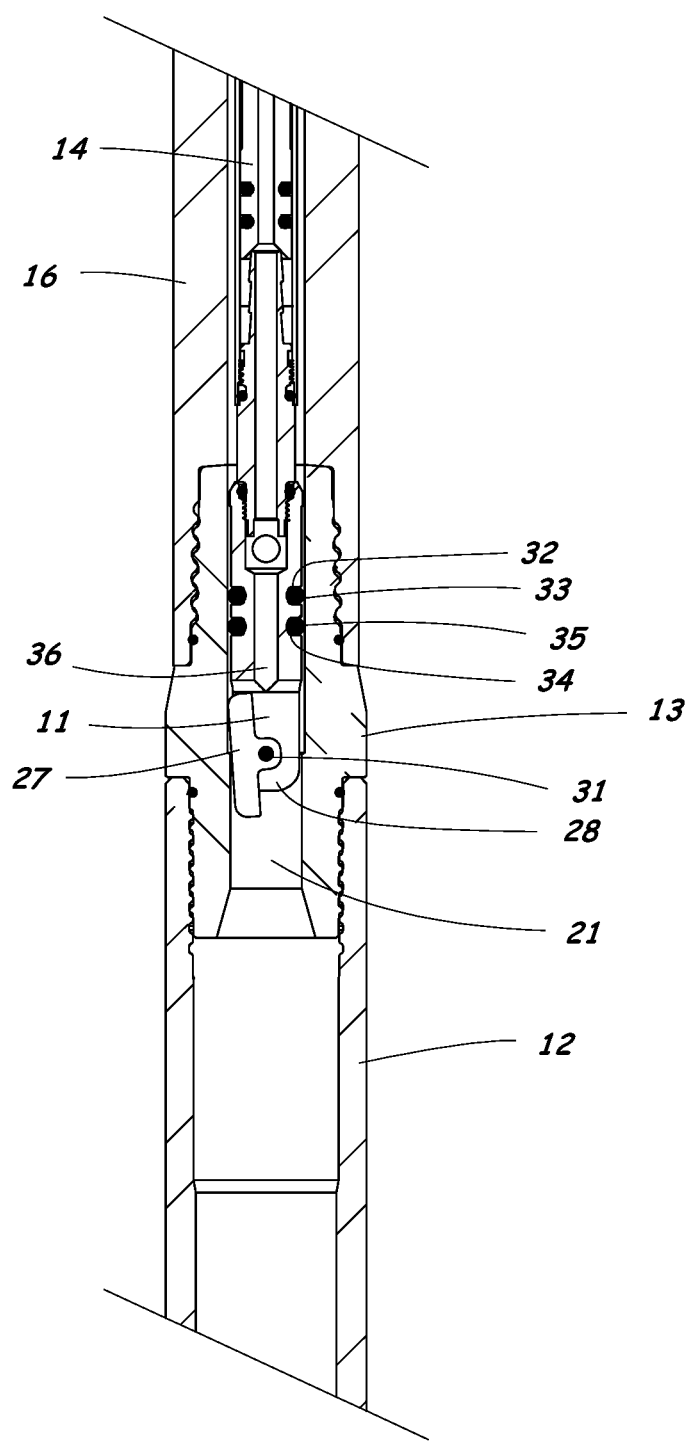
FIG. 3 is a detail elevation view of the screen point groundwater sampling system showing a mechanical pump being inserted downwardly through the inner bore of the probe rod and the inner bore of the drive head.
Figure 4:
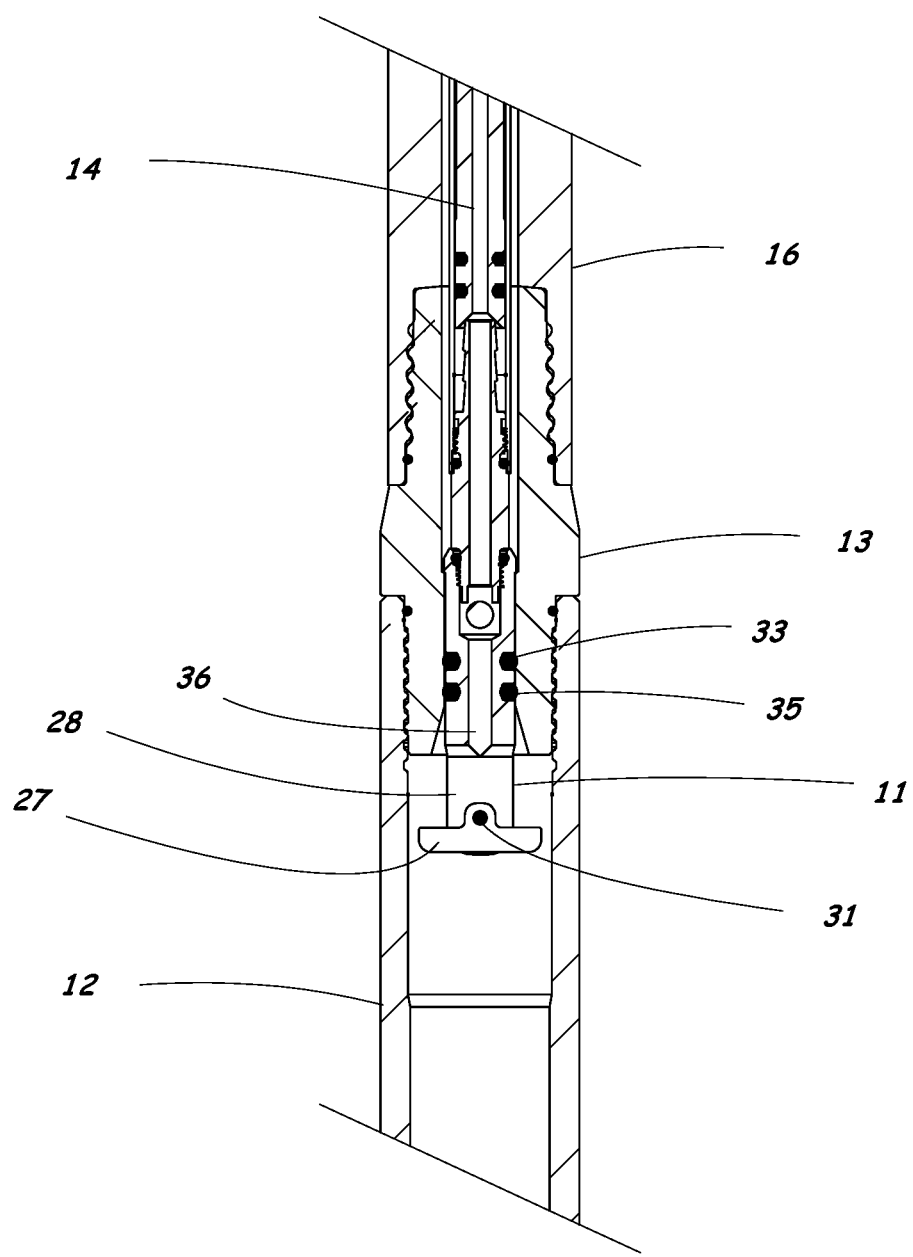
FIG. 4 is a detail elevation view of the screen point groundwater sampling system with the mechanical pump fully inserted and a latching tool deployed into a latched condition.
Figure 5:
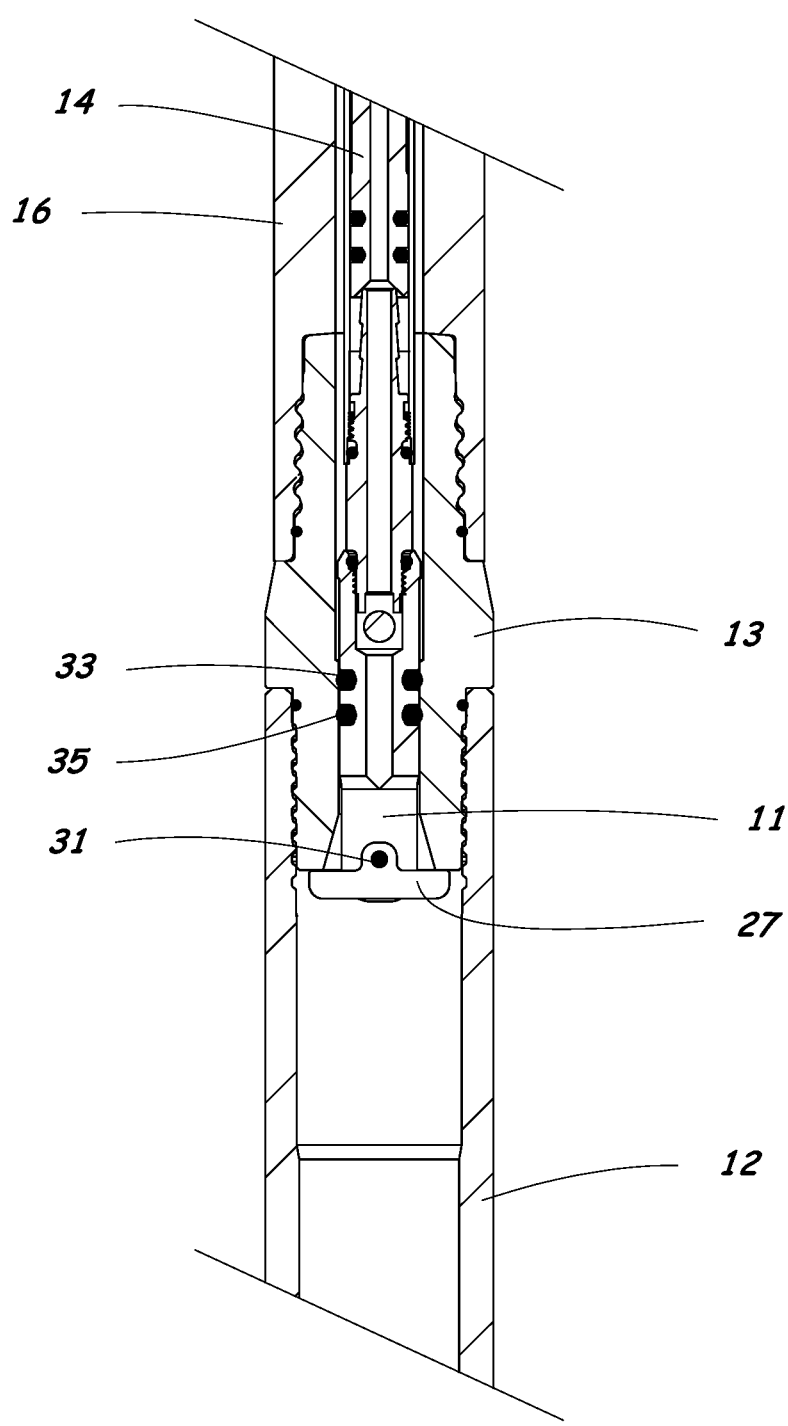
FIG. 5 is a detail view of the screen point groundwater sampling system with the mechanical pump raised into a position in which a latch of the latching tool engages a lower surface of the drive head.

FIG. 1 illustrates a screen point groundwater sampling system 10 according to the present invention. The system 10 includes an elongated screen sheath assembly 12, a drive head 13, a latching tool 11, a mechanical pump 14, a sample tubing 15, and a probe rod 16. The elongated screen sheath assembly 10 can be, for example, as described in Applicant's prior U.S. Pat. Nos. 5,503,031, 5,612,498 and 5,635,653, which are incorporated herein by reference. The screen sheath assembly can also be in the form of the Screen Point 16 system available commercially from Geoprobe Systems, Salina, Kansas. The screen sheath assembly 12 can be an elongate hollow screen received within a housing and capable of being placed in a stowed position within the housing during driving of the device into the ground, and in a deployed position where it extends out of the lower end of the housing to collect groundwater.

The mechanical pump 14 used in the present invention can be, for example, the pump described in Applicant's prior U.S. Pat. No. 6,877,965, which is incorporated herein by reference. The mechanical pump 14 can also be in the form of the various Mechanical Bladder Pumps and Mechanical Syringe Pumps available commercially from Geoprobe Systems, Salina, Kansas.

The latching tool 11 of the present invention provides an improvement over the prior art by allowing the mechanical pump 14 to be secured to the drive head 13 as described below, and by providing a sealed barrier between the groundwater sample being collected and the static water in the probe rod 16.

The drive head 13 has an upper male threaded portion 17 adapted to be attached to a lower female threaded portion 18 of the probe rod 16, and a lower male threaded portion 19 adapted to be attached to an upper female threaded end 20 of the elongated screen sheath 12. The drive head 13 has an inner bore 21 with an upper portion 22 having a first diameter, and a lower portion 23 having a second diameter which is smaller than the first diameter. An inner shoulder 24 is defined by the transition in diameters between the upper portion 22 and lower portion 23 of the inner bore 21.

The inner shoulder 24 of the drive head 13 is arranged to engage an abutting surface 25 on the latching tool 11 to limit downward movement of the latching tool 11 through the drive head 13. The abutting surface on the latching tool 11 is an outer shoulder arranged to engage the inner shoulder 24 of the drive head 13 to limit downward movement of the latching tool 11 through the inner bore 21 of the drive head 13.

The latching tool 11 is attached to a lower end 26 of the mechanical pump 14 for securing the mechanical pump 14 to the drive head 13 in a coupled condition, and also to allow the mechanical pump 14 to be actuated. The latching tool 11 has a latch member 27 for engaging the drive head 13 upon insertion of the latching tool 11 into the inner bore 21 of the drive head 13. The latch member 27 is pivotally mounted to a fork structure 28 with aligned bores 29 at the lower end of the latching tool 11. A latch pin 31 extends through the aligned bores 29 to pivotally mount the latch member 27. The latch pin 31 is a frangible element, as explained below.

The latch member 27 is moveable between a first vertical position (FIG. 3) for allowing downward insertion of the latching tool 11 through the inner bore 21 of the drive head 13, and a second horizontal position (FIGS. 4 and 5) for restricting upward movement of the latching tool 11 relative to the drive head 13. The latch member 27 is held in the first vertical position (FIG. 3) by engagement with the inner bore 21 of the drive head 13 during insertion. The latch member 27 is moveable from the first vertical position (FIG. 3) to the second horizontal position (FIG. 4) due to gravitational forces acting on the latch member 27. More specifically, the latch member 27 has a pivot axis (the latch pin 31) and a center of gravity, and the center of gravity moves relatively lower with respect to the pivot axis when the latch member 27 moves from the first vertical position to the second horizontal position.

The latch pin 31 is frangible to allow the mechanical pump 14 to be removed from the drive head 13 upon applying sufficient vertical force to the latching tool 11 in an upward direction to shear the latch pin 31. The latch pin 31 can be formed of a length of nylon line, such as string trimmer line. For example, an extruded nylon monofilament string trimmer line having a 0.065 inch diameter has been demonstrated as suitable for use as the frangible latch pin 31.

The latching tool 11 has a generally cylindrical outer surface with at least one annular groove 32 and at least one O-ring seal 33 fit within the annular groove 32. In the illustrated embodiment, the latching tool 11 has first and second annular grooves 32, 34, and first and second O-ring seals 33, 35 fit within the first and second annular grooves 32, 34, respectively. The O-ring seals 33, 35 create a seal between the outer surface of the latching tool 11 and the inner bore 21 of the drive head 13.

The latching tool 11 has an inner bore 36 for providing a fluid passage from the elongated screen sheath 12 through the drive head 13 to the mechanical pump 14. The static water often found in the probe rod 16 above the drive head 13 is sealed from contaminating the sampled groundwater by the O-ring seals 33, 35 between the latching tool 11 and the drive head 13.

The screen point groundwater sampling system 10 according to the first embodiment of the invention is explained above. A method of sampling groundwater using the screen point groundwater sampling system 10 will now be described.

The screen point sampling system 10 is driven into a ground formation to a desired sampling depth. The screen point sampling system 10 includes the drive head 13 connected between the lower end 18 of the probe rod 16 and the upper end 20 of the elongated screen sheath 12. The screen is deployed in a known manner from the elongated screen sheath 12 to allow ground water into the sampling system 10. The latching tool 11 and mechanical pump 14 are then inserted down through the bore of the probe rod 16 until the latching tool 11 engages a downward limiting structure 24 on the drive head 13. An outer surface of the latching tool 11 is sealed with the inner bore 21 of the drive head 13, and the latch member 27 of the latching tool 11 flips into position to restrict upward movement of the latching tool 11 relative to the drive head 13.

With the latch member 27 of the latching tool 11 engaged with the drive head 13, a first lower part 37 of the mechanical pump 14 is held stationary relative to the drive head 13, while a second upper part 38 of the mechanical pump 14 can be reciprocated by vertical forces applied through the sample tubing 15 to the second part 38 of the mechanical pump 14. The mechanical pump 14 is actuated to draw groundwater upwardly through the inner bore 36 of the latching tool 11 while the outer surface of the latching tool 11 remains sealed with the inner bore 21 of the drive head 13. The latch member 27 restricts upward movement of the latching tool 11 relative to the drive head 13.

Figure 6:
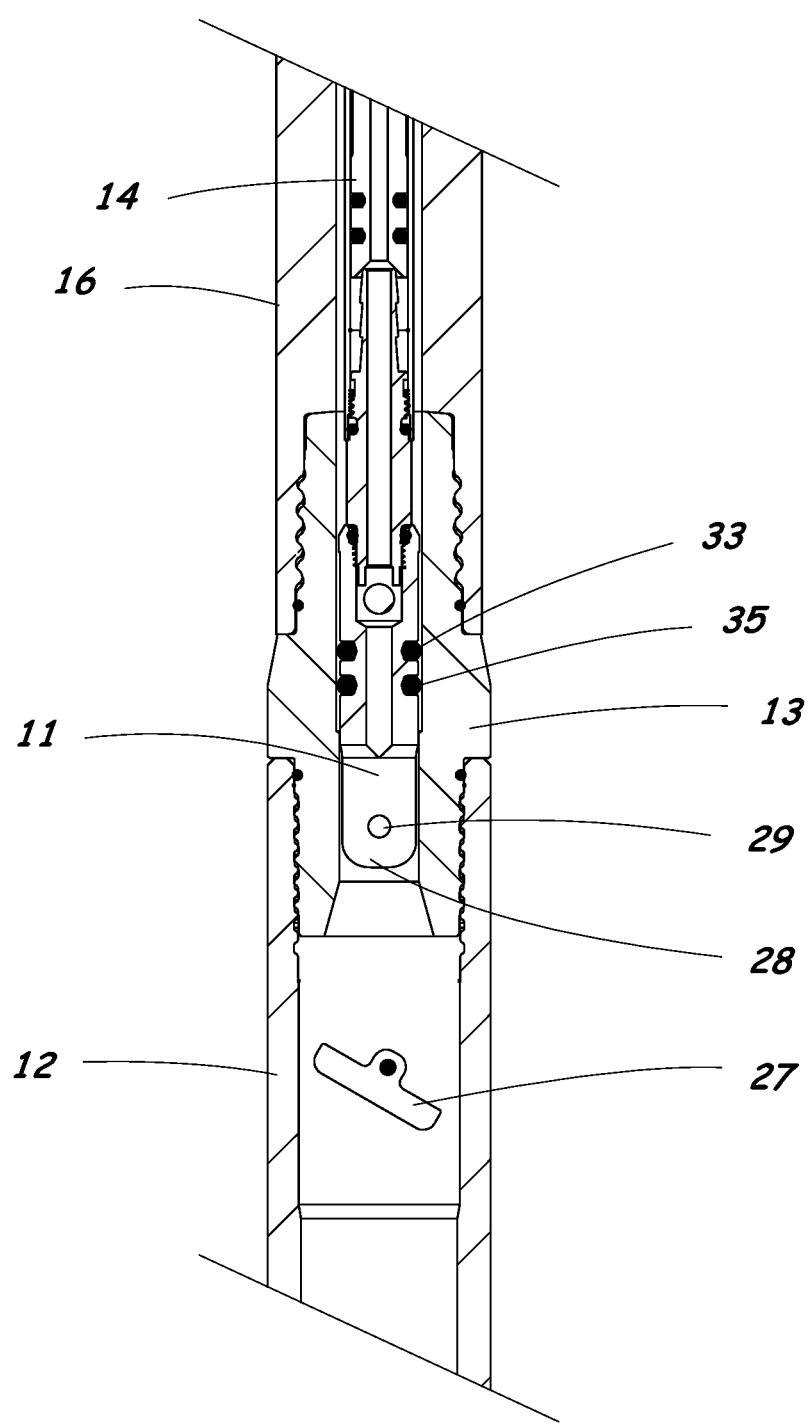
FIG. 6 is a detail view of the screen point groundwater sampling system showing the mechanical pump in the process of being removed from the drive head by applying a sufficient vertical lifting force to shear a frangible structure of the latching tool.
Figure 7:
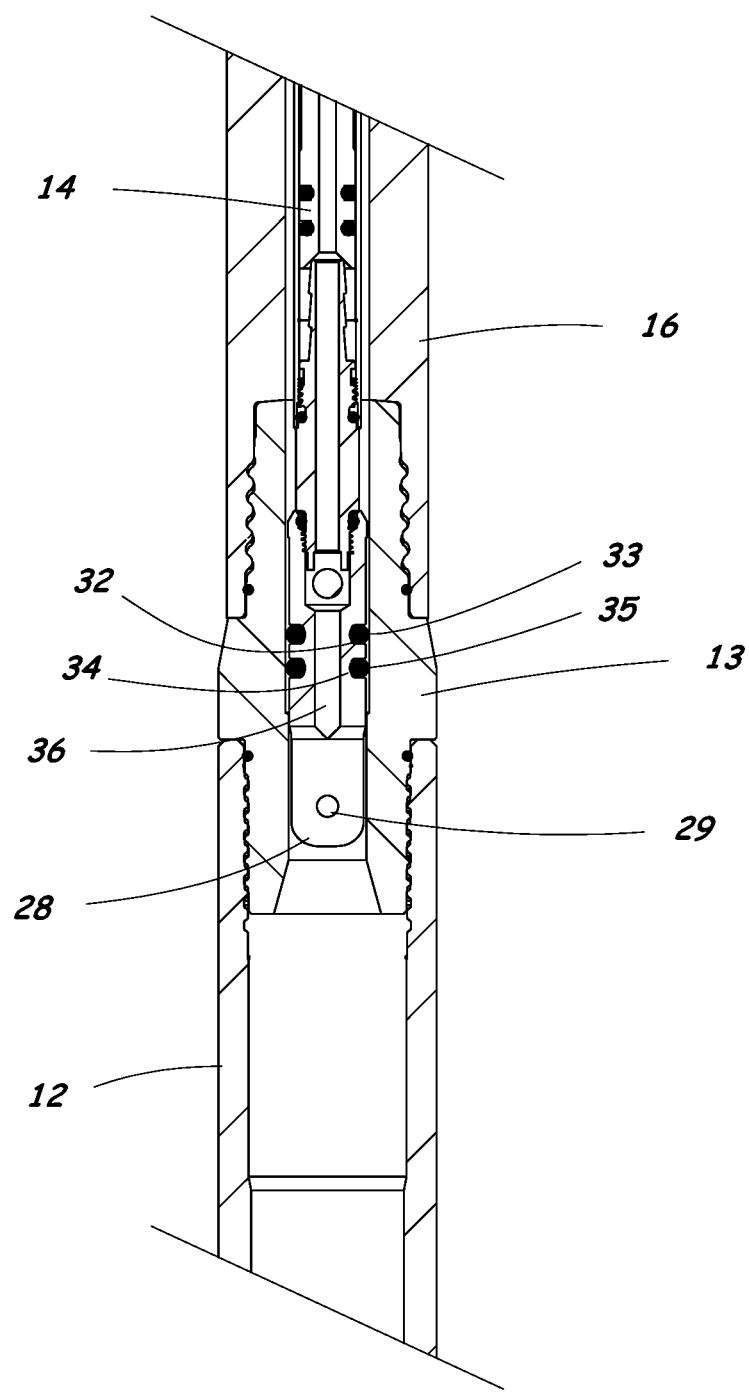
FIG. 7 is another detail view of the screen point groundwater sampling system showing the mechanical pump and latching tool being removed from the drive head.
Figure 8:
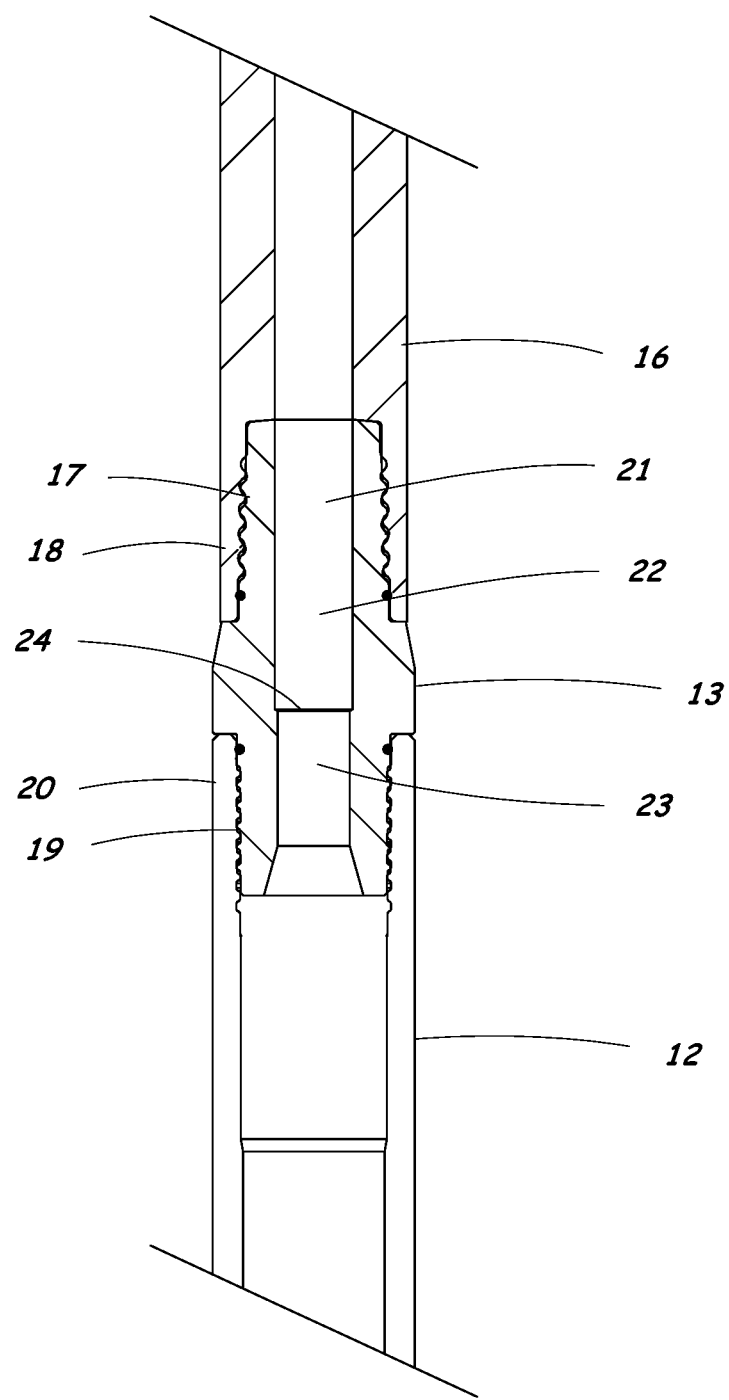
FIG. 8 is a detail view of the screen point groundwater sampling system with the mechanical pump and latching tool removed from the drive head.

When the groundwater pumping is completed, the mechanical pump 14 and latching tool 11 can be removed from the probe rod 16 and drive head 13 by applying a sufficient vertical force to the sample tubing 15 to cause the latch pin 31 of the latching tool 11 to shear. The latch member 27 then drops away (as shown in FIG. 6), and the mechanical pump 14 and latching tool 11 can be pulled upwardly out of the probe rod 16.

Figure 9:
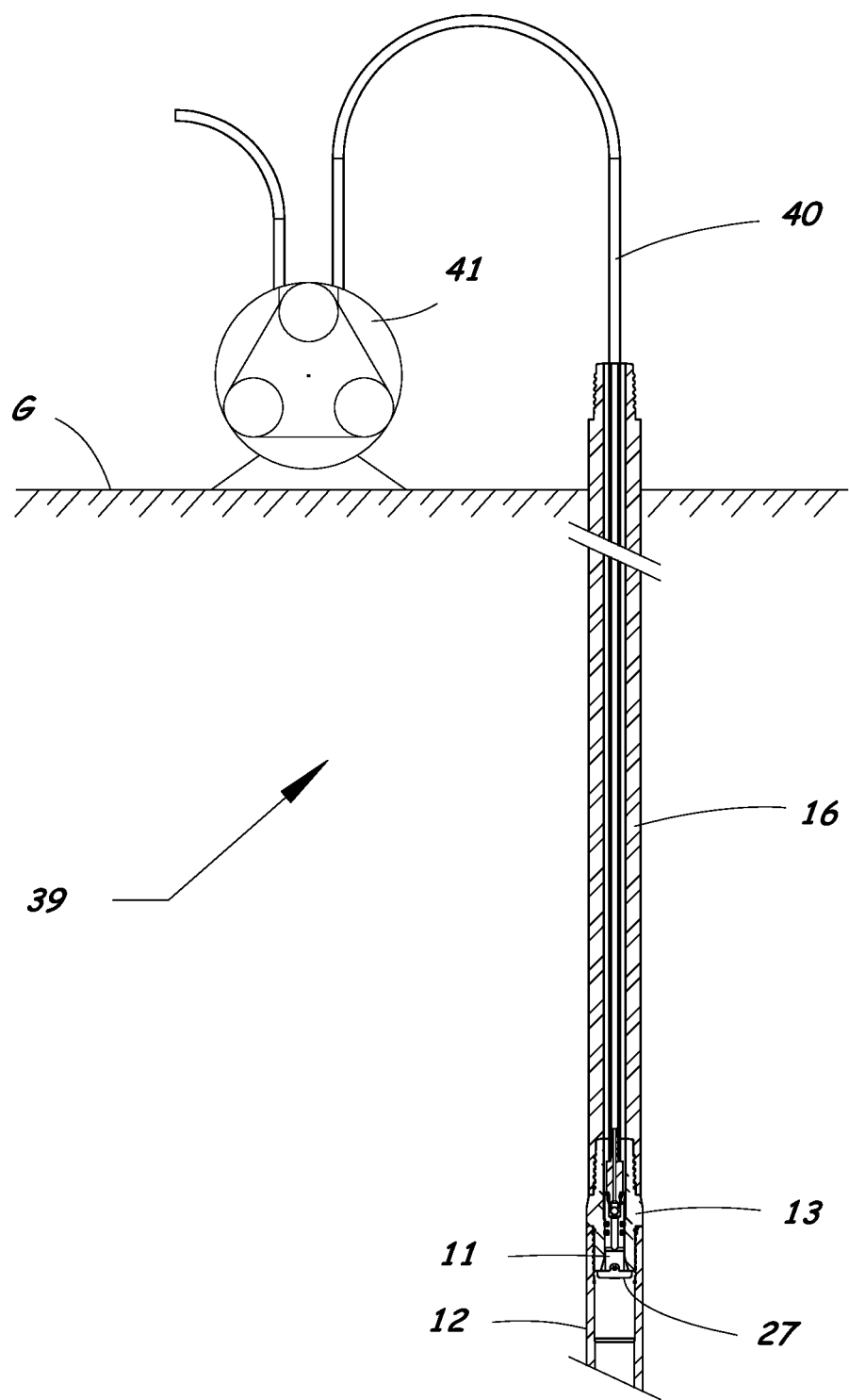
FIG. 9 is an elevation view of a screen point groundwater sampling system according to another embodiment of the invention in which a sample tubing is inserted through the probe rod and latched to the drive head, and a pump located at the ground surface is used to draw groundwater through the sample tubing from below the drive head.

A screen point groundwater sampling system 39 according to a second embodiment of the invention is illustrated in FIG. 9. In this embodiment, the latching tool 11 is secured to a lower end of a sample tubing 40, and a groundwater pump 41 connected to the other end of the sample tubing 40 is positioned at the ground surface G. The groundwater pump 41 at the ground surface is used instead of a mechanical pump located within the probe rod 16. This embodiment is suitable for shallow groundwater pumping that can be accomplished within the normal limits for lifting water by suction.

In this embodiment, the sample tubing 40 itself serves as the inserted structure to which the latching tool 11 is attached, instead of a mechanical pump located within the probe rod 16. The latching tool 11 otherwise has the same structure as described above and illustrated in the drawings of the first embodiment.

In operation, the sample tubing 40 is inserted downwardly through the bore of the probe rod 16 until the shoulder 25 on the outer surface of the latching tool 11 abuts the shoulder 24 on the inner bore of the drive head 13. The O-rings 33, 35 on the latching tool 11 create a fluid-tight seal between the latching tool 11 and the inner bore 21 of the drive head 13. With the sample tubing 40 and latching tool 11 fully inserted into the inner bore 21 of the drive head 13, the pump 41 at the ground surface G can then be activated to draw groundwater through the inner bore 36 of the latching tool 11. Once the sampling is completed, the sample tubing 40 can be lifted with sufficient force to shear the latch pin 31 and remove the latching tool 11 and the sample tubing 40 from the drive head 13.

The present invention overcomes the limitations with conventional screen point sampling systems by isolating the screen point sampler 12 from the rod string 16 above the sampler, thereby isolating the water sample from rod leakage and unswept rod water.

The latching tool 11 of the present invention is connected to the mechanical pump 14 or to an end of a length of sample tubing 40 lowered down the bore of direct push drive rods 16 and inserted into the drive head 13 of a direct push groundwater sampler. The latching tool 11 is equipped with a latching system so that insertion of the latching tool 111 into the drive head 13 automatically activates the latch member 27, and the latching tool 111 cannot be removed from the drive head 13 without application of sufficient tension on the sample tubing 15, 40 to overcome the holding force of the latch member 27.

Insertion of the latching tool 11 into the drive head 13 creates a watertight seal between the sample tubing 15, 40 and the drive head 13 of the groundwater sampler. This watertight seal excludes water contained in the drive rods 16 or water which may leak into the drive rods 16 during the sampling event from entering the drive head 13 and thereafter mixing with or contaminating the groundwater being sampled from the sampler screen 12.

As described above with reference to the first embodiment of the invention, one application of the latching tool 11 is to use it as the lower member of a linear actuated mechanical pump 14 which is inserted down the bore of the drive rods 16 between the lower end of the sample tubing 15 and the upper end of the latching tool. This mechanical pump 14 is actuated by vertical oscillation of the sample tubing, which can be accomplished manually or mechanically using a suitable drive mechanism, such as the motor and reciprocating drive mechanism 45 shown in FIG. 2. For groundwater sampling with this type of mechanical pump 14 the holding force of the latching tool 11 must exceed the upward actuation force of the pump 14.

When groundwater sampling is finished at a particular depth interval in the ground then it is desirable to remove the sample tubing 15 and mechanical pump 14 from the bore of the rods 16 prior to extraction of the rods 16 from the ground. This is accomplished by pulling up on the sample tubing 15 with sufficient force to overcome the shear strength of the latch pin 31 of the latching tool 11, thereby causing the latch member 27 to break away from the latching tool 11 and release the latching tool 11 and attached sample tubing 15 from the drive head 13. Removal of the sample tubing 15 allows insertion of other tubing down the rod bore to accomplish retraction grouting of the bore hole. Removal of the sample tubing 15 and the latching tool 11 also reduces the effort required to extract the rods 16 and groundwater sampler 12.

While the invention has been described in connection with specific embodiments thereof, it is to be understood that this is by way of illustration and not of limitation, and the scope of the appended claims should be construed as broadly as the prior art will permit.

What is claimed is:

1. A latching system for a groundwater sampling system, comprising:
   a drive head comprising an upper threaded portion adapted to be attached to a lower end of a probe rod, a lower threaded portion adapted to be attached to an upper end of an elongated screen sheath, and an inner bore; and
   a latching tool attached to a lower end of an inserted structure for securing the inserted structure to the drive head, said latching tool comprising a latch for engaging the drive head upon insertion of the latching tool into the inner bore of the drive head.

2. The latching system according to claim 1, wherein said inserted structure comprises a mechanical pump, and said latching tool is arranged to secure the mechanical pump to the drive head to allow the mechanical pump to be actuated.

3. The latching system according to claim 1, wherein the inner bore of the drive head comprises an upper portion, a lower portion and an inner shoulder defined between the upper and lower portions for engaging an abutting surface on the latching tool to limit downward movement of the latching tool through the drive head.

4. The latching system according to claim 3, wherein the upper portion of the inner bore has a first diameter and the lower portion has a second diameter which is smaller than the first diameter, and the inner shoulder in the inner bore is defined by the transition between the first and second diameters.

5. The latching system according to claim 3, wherein said abutting surface on the latching tool comprises an outer shoulder arranged to engage the inner shoulder of the drive head.

6. The latching system according to claim 1, wherein said latching tool has a cylindrical outer surface, and at least one O-ring seal that fits in a groove for creating a seal between the outer surface of the latching tool and the inner bore of the drive head.

7. The latching system according to claim 6, wherein said at least one O-ring seal comprises a pair of O-ring seals that fit in respective grooves in the outer surface of the latching tool.

8. The latching system according to claim 6, wherein said latching tool further comprises an outer shoulder for engaging a structure in the inner bore of the drive head to limit downward movement of the latching tool through the drive head.

9. The latching system according to claim 1, wherein said latching tool further comprises an outer shoulder for engaging a structure in the inner bore of the drive head to limit downward movement of the latching tool through the drive head.

10. The latching system according to claim 1, wherein said latching tool comprises an inner bore for providing fluid passage from the elongated screen sheath through the drive head to the inserted structure.

11. The latching system according to claim 1, wherein said latch comprises a latch member pivotally mounted adjacent to a lower end of the latching tool.

12. The latching system according to claim 11, wherein said latch member is moveable between a first vertical position for allowing downward insertion of the latching tool through the inner bore of the drive head and a second horizontal position for restricting upward movement of the latching tool relative to the drive head.

13. The latching system according to claim 12, wherein said latch member is held in said first vertical position by engagement with the inner bore of the drive head during insertion.

14. The latching system according to claim 13, wherein said latch member is moveable from said first vertical position to said second horizontal position by gravity.

15. The latching system according to claim 14, wherein said latch member has a pivot axis and a center of gravity, and wherein said center of gravity moves relatively lower with respect to said pivot axis when said latch member moves from said first vertical position to said second horizontal position.

16. The latching system according to claim 15, wherein the lower end of the latching tool comprises a fork with aligned bores and a latch pin extending through the aligned bores to pivotally mount the latch member.

17. The latching system according to claim 16, wherein said latch pin is shearable to allow the inserted structure to be removed from the drive head upon applying sufficient vertical force to the latching tool in an upward direction to shear the latch pin.

18. The latching system according to claim 1, wherein said latch comprises a latch member secured to the latching tool by a shearable structure that allows the inserted structure to be removed from the drive head upon applying sufficient vertical force to the latching tool in an upward direction to shear the shearable structure.

19. The latching system according to claim 18, wherein said shearable structure comprises a length of string trimmer line.

20. The latching system according to claim 18, wherein said shearable structure comprises nylon line.

21. The latching system according to claim 1, wherein said inserted structure comprises a sample tubing inserted through the probe rod, said sample tubing being connected to a pump for drawing fluid through an inner bore of the latching tool.

22. A latching tool for securing an inserted structure to a drive head in a screen point sampling system, the latching tool comprising:
   a main body having a generally cylindrical outer surface with at least one groove for receiving an O-ring seal to create a seal between the outer surface of the latching tool and an inner surface of the drive head;

an outer shoulder for engaging a structure in the inner bore of the drive head to limit downward movement of the latching tool through the drive head;

an inner bore for providing fluid passage from an elongated screen sheath below the drive head to the inserted structure; and a pivotally mounted latch member adapted to engage the drive head upon insertion of the latching tool into the inner bore of the drive head.

23. The latching tool according to claim 22, wherein said inserted structure comprises a mechanical pump, and said latching tool is arranged to secure the mechanical pump to the drive head to allow the mechanical pump to be actuated.

24. The latching tool according to claim 22, wherein said inserted structure comprises a sample tubing connected to a pump for drawing fluid through an inner bore of the latching tool.

25. The latching tool according to claim 22, wherein said pivotally mounted latch member is moveable between a first vertical position for allowing downward insertion of the latching tool through the inner bore of the drive head and a second horizontal position for restricting upward movement of the latching tool relative to the drive head.

26. The latching tool according to claim 25, wherein said latch member is held in said first vertical position by engagement with the inner bore of the drive head during insertion, and wherein said latch member is moveable from said first vertical position to said second horizontal position by gravity.

27. The latching tool according to claim 22, wherein said latch member is secured to the latching tool by a shearable structure that allows the inserted structure to be removed from the drive head by applying sufficient vertical force to the latching tool in an upward direction to shear the shearable structure.

28. A method of sampling groundwater, comprising:

driving a screen point sampling assembly into the ground, the screen point sampling assembly comprising a drive head connected between a lower end of a probe rod and an upper end of an elongated screen sheath, the drive head having an inner bore;

deploying a screen from the elongated screen sheath;

inserting a structure with a latching tool downward through the probe rod until the latching tool engages a downward limiting structure on the drive head, an outer surface of the latching tool is sealed with the inner bore of the drive head, and a latch of the latching tool flips into a position to restrict upward movement of the latching tool relative to the drive head;

actuating a pump to pump groundwater through an inner bore of the latching tool while the outer surface of the latching tool remains sealed with the inner bore of the drive head and the latch restricts upward movement of the latching tool relative to the drive head; and removing the inserted structure and latching tool from the probe rod and drive head by applying sufficient force to cause a shearable structure on the latching tool to shear.

29. The method of sampling groundwater according to claim 28, wherein said step of inserting a structure comprises inserting a mechanical pump into the probe rod along with the latching tool, and said step of actuating a pump comprises using the latching tool to hold a first part of the mechanical pump stationary relative to the drive head while a second part of the mechanical pump is reciprocated by vertical forces applied through a sample tubing connected to the second part of the mechanical pump.

* * * * *